United States Patent

Valducci

[11] Patent Number: 5,149,542
[45] Date of Patent: Sep. 22, 1992

[54] COATING MEMBRANE AND COMPOSITIONS PREPARED THEREFROM

[76] Inventor: Roberto Valducci, Via del Sole, 4, Savignano sul Rubicone, Italy, 47039

[21] Appl. No.: 194,992
[22] PCT Filed: Sep. 29, 1987
[86] PCT No.: PCT/IT87/00085
    § 371 Date: May 2, 1988
    § 102(e) Date: May 2, 1988
[87] PCT Pub. No.: WO88/02253
    PCT Pub. Date: Apr. 7, 1988

[30] Foreign Application Priority Data

Sep. 30, 1986 [IT] Italy ................... 3530 A/86

[51] Int. Cl.$^5$ .......... A61K 9/58; A61K 9/62; A61K 9/22; A61K 9/48
[52] U.S. Cl. .......... 424/493; 424/451; 424/470; 424/497; 424/498
[58] Field of Search ............ 424/470, 497, 498, 493, 424/451, 465

[56] References Cited

U.S. PATENT DOCUMENTS

| | | | |
|---|---|---|---|
| 2,828,206 | 3/1958 | Rosenberg | 424/498 |
| 3,078,216 | 2/1963 | Greif | 424/458 |
| 3,080,294 | 3/1963 | Shepard | 424/498 |
| 3,432,593 | 3/1969 | Shepard | 424/498 X |
| 3,492,397 | 1/1976 | Peters et al. | 424/498 X |
| 3,922,339 | 11/1975 | Shear | 424/498 |
| 4,341,759 | 7/1982 | Bogentoft et al. | 424/498 |
| 4,572,833 | 2/1986 | Pedersen et al. | 424/498 |

FOREIGN PATENT DOCUMENTS

| 0123470 | 10/1984 | European Pat. Off. | 424/498 |
|---|---|---|---|
| 1044572 | 10/1966 | United Kingdom | 424/498 |

Primary Examiner—Thurman K. Page
Attorney, Agent, or Firm—Darby & Darby

[57] ABSTRACT

Controlled release pellets consisting of an inert material, a medicament layer and a coating membrane of a mixture or stearic acid and ethyl cellulose or of parrafin and methacrylic acid copolymer.

13 Claims, 1 Drawing Sheet

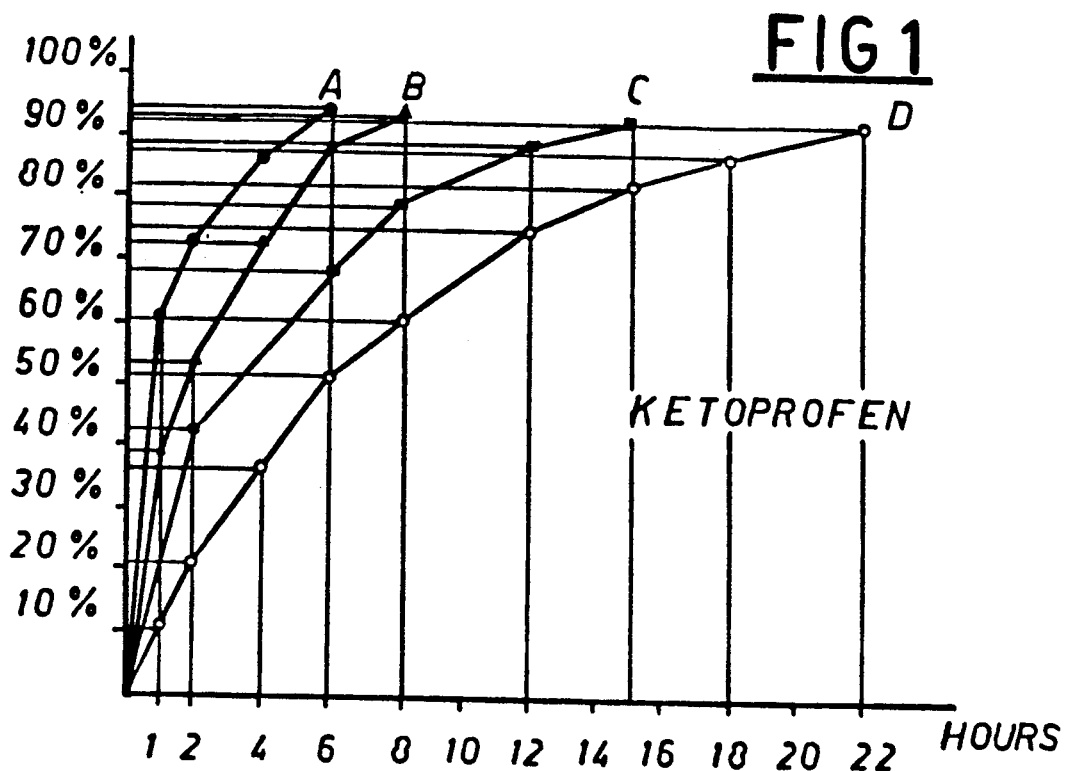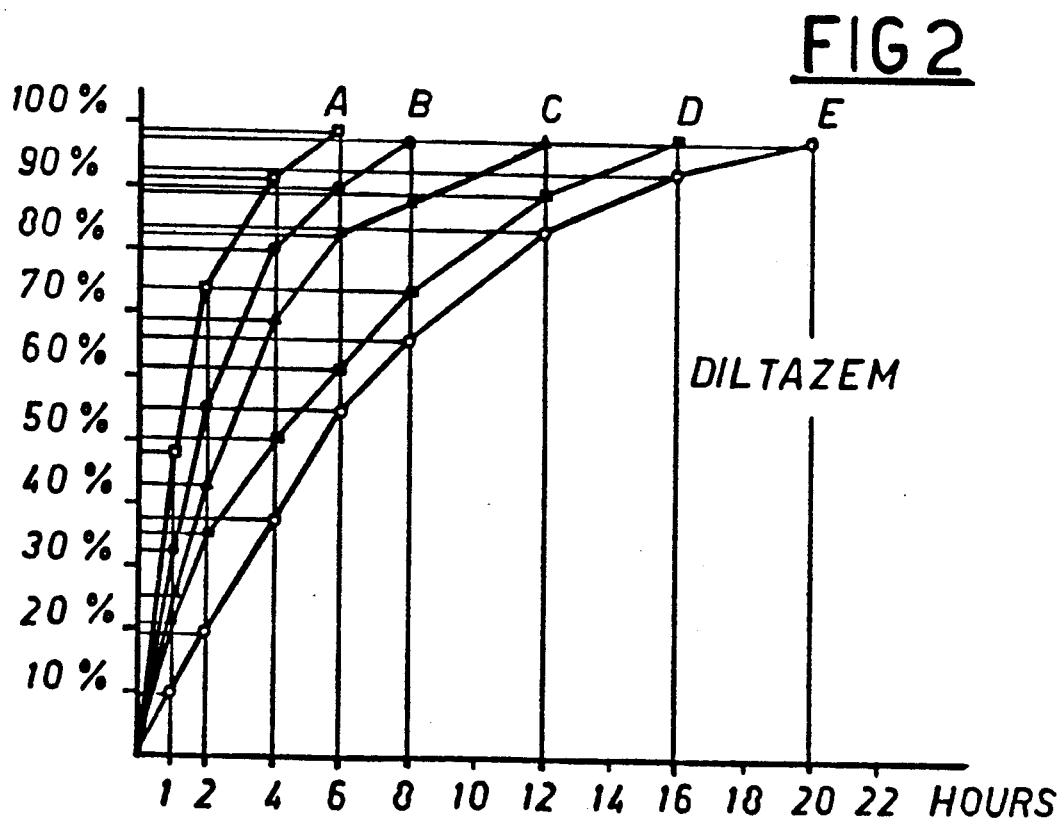

COATING MEMBRANE AND COMPOSITIONS PREPARED THEREFROM

This invention relates to a coating membrane for pharmaceutical and industrial purposes and to compositions prepared therefrom. More particularly it relates to a coating membrane for the controlled release of an active ingredient which may be of pharmaceutical, veterinary, synthetic or extractive type, and to compositions containing said coated active ingredient.

In the pharmaceutical field, the production of sustained release microgranules is known (see for example EP 123,470 and 122,077).

The preparation involves the application of the active ingredient on a spherical nucleus having a diameter of from 0.2 to 2 mm by means of a particular binding agent, or a spherical nucleus of active ingredient with or without binding agent may be prepared. Then a semipermeable membrane is applied, which allows the diffusion of the drug over a controlled period of time or it disgregates over a well-established period of time releasing the drug.

The membrane normally used and described in several patents consists of: shellac, methacrylic acid copolymers, ethylcellulose, ethylcellulose phtalate, hydroxypropyl methylcellulose, cellulose acetophtalate, etc. The abovementioned and currently used membranes are also of natural source, such as shellac, and thus of indefinite composition. As a consequence, the amounts used to obtain identical coating notably change from time to time and give, therefore, stability problems. The productions from batch to batch are thus difficult, and often it is not possible to obtain the same release pattern.

Moreover, it is very difficult to reach a zero order release or a release over a controlled period of time according to the drug needs.

In the pharmaceutical field, the purpose of the sustained release formulations is to obtain a 12 hours therapeutically active hematic level with consequent posology of two daily administrations, or else a 24 hours hematic level with administration of a sole capsule a day. In order to achieve said results, the drug release has to be more or less delayed according to the characteristics half-life of each drug.

It has now been found that, modifying the amount of the applied membrane or the ratios between two components, it is possible to obtain sustained releases from 4–6 hours up to 18–22 hours and higher, as shown in FIG. 1 for ketoprofen (ethylcellulose/stearic acid membrane) and in FIG. 2 for diltiazem hydrochloride (paraffin/methacrylic acid copolymers membrane).

This technological flexibility allows to choose the most suitable in vitro release for obtaining the in vivo blood level which provides the pharmaceutical effect over a desired period of time.

BRIEF DESCRIPTION OF THE DRAWINGS

FIGS. 1 and 2 are graphs of the rate of release versus time for Ketoprofen and Diltiazem.

Several tests have shown a very good reproducibility from batch to batch and good stability. Membranes from synthetic products with a well-definite molecular composition, and often reported in International Pharmacopeias, provide an improved purity, as shown by the analytical tests.

These new membranes, like paraffin, have for their own nature a very low chemical affinity for the products which have to be coated. In this way, a very good compatibility does exist between membrane and product to be coated, and a good time stability may be achieved.

Accordingly, the present invention relates to the use, as semipermeable or breakable membranes, of lipophilic compounds alone or in admixture with a suitable hardening agent. More particularly the present invention relates to a coating membrane for pharmaceutical, cosmetic, veterinary, synthetic and extractive substances and to the compositions prepared therefrom.

In a further embodiment, the invention provides also a method for preparing said compositions, which comprises coating inert material pellets with a first layer of a therapeutically active compound and applying then thereon a second layer consisting of a lipophilic substance, alone or in admixture with a hardening agent.

In the compositions of the present invention, the inert pellets comprise preferably sucrose and starch.

The substances used as lipophilic membranes are the following:

A) Fatty acids containing from 12 to 20 carbon atoms, such as palmitic acid, and/or paraffin (USP XXI, page 1584).

The compounds utilized for having hardening action are selected from:

B) Ethylcellulose Hercules with Ethoxy groups 44.5 to 50%.

C) Hydroxypropylmethylcellulose (Dow Chemicals type E Premium, viscosity from 50 to 4000 cps).

D) Hydroxyethylcellulose (Hercules Natrosol, viscosity from 180 to 250 cps).

E) Hydroxypropylcellulose (Hercules, Klucel, viscosity from 150 to 6500 cps).

F) Hydroxypropylmethylcellulosephtalate (Shinetsu Chemicals, Tokyo).

G) Methylcellulose (Dow Chemical-Methocel Premium, viscosity from 15 to 4000 cps Henkel, Viscontran).

H) Methacrylic acid copolymers (Rohm Pharma GmbH) Eudragit E, L, S, RS, RL, E 30D, L 30D, RL 30D, RS 30D type.

I) Cellulose Acetophtalate (Kodak).

J) Polyethyleneglycol (Hoechst PEG, molecular weight from 300 to 35000).

K) Polyvinylacetate (PVA) (Colorcon UK) (Canada Packers Chemicals, Canada).

L) Polyvinylpyrrolidone (PVP) (BASF, Kollidon, k values from 10 to 95).

M) Hydroxybutylcellulose (Dow Chemicals, viscosity 12000 cps).

N) Carboxymethylcellulose sodium (Henkel Dehydazol, viscosity 400–15000 cps).

O) Polyvinylacetophtalate (PVAP) (colorcon, UK) (Canada Packers Chemicals, Canada).

All the hardening agents mentioned above are preferably dissolved in ethanol, acetone, methylene chloride or in other organic solvents at room temperature or at a temperature corresponding to the boiling point of the employed solvent. In this way, 0.1% to saturated solutions may be obtained. The hardeners can be dissolved alone or mixed each other in all the proportions.

The lipophilic substances are dissolved in the above solvents or they are melted. They can be used alone or in admixture each other, and they are applied melted or in solution.

Tests carried out on theophylline with stearic acid alone as membrane, show a faster release in comparison with that obtained with the same amount of stearic acid but added with hydroxypropylmethylcellulose. Adding hardening agents to the lipophilic compounds, a more flexible and less rapid release over a controlled period of time may be achieved. In order to obtain mechanically harder and more stable membranes, the lipophilic compounds should be blended with the hardening agents in solution, where possible, or in alternate layers.

In this case, the preferred ratio lipophilic compound to hardening agent is of from 0.1 to 100% for the lipophilic substance and of from 0.9 to 99.9% for the hardener. The application of the membranes on microgranules or other material which has to be coated, is done for achieving: a slow release of the coated material, gastroprotection, separation of incompatible substances, reduction of the chemical reactivity, physical separation, handling improvement, to eliminate bad smell and taste, stability improvement. The melted or solubilized membrane is applied on the material which has to be coated by means of high pressure pump in order to subdivide it in microdrops.

Said procedure is carried out in stainless steel coating pans with variable rotation speed from 3 to 40 rpm according to the diameter, with a fluid bed apparatus (uni-glatt) or in fast mixers, such as Loeding type or the like. The evaporation of the solvents utilized in the process, is performed in thermostatic dryers or under vacuum at a temperature of from 30° to 45° C.

The lipophilic compounds, alone or mixed each other, and with possible addition of hardening agents, can also be used with spray dry or spray cooling techniques.

The following examples illustrate the invention and facilitate its understanding.

EXAMPLE 1

On 19 kg of neutral pellets, consisting of 75% w/w of sucrose and 25% (w/w) of starch and placed in a stainless steel coating pan, ketoprofen was applied (53.5 kg) with a 20% (w/w) alcoholic solution (ethanol) of polyethylene glycol (MW 4000). After drying, a 4.5% (w/w) alcoholic solution of ethylcellulose (with 44.5 to 50% of ethoxy groups) and 7.5% of stearic acid was applied, with addition of 2.70 kg of talc.

After drying, the product contained 2.23 kg of stearic acid (NF XVI, page 1611) and 1.33 kg of ethylcellulose. The release test, carried out according to USP XXI, Apparatus No. 1, at 150 rpm and with 900 ml of juice of pH 7.2, provided the results reported in FIG. 1, curve D. The curves A to C were obtained with formulations having increased amounts of membrane. With said formulation, capsules containing from 50 to 250 mg of ketoprofen may be prepared.

EXAMPLE 2

82.00 kg of paracetamol were placed in a Loeding type mixer, and under stirring 12.40 kg of stearic acid (NF XVI, page 1611), melted and blended with 25.00 kg of a 10% (w/w) ethanolic solution of ethylcellulose (44.5–50% ethoxy groups), were added at a temperature of 50°-60° C.

The mass was stirred for 10-15 minutes and then dried in a thermostatic box at 35°-45° C. The granulate thus obtained had a masked taste and can be used in monodose bags or in other pharmaceutical forms. The granulate was mixed with 3.00 kg of magnesium stearate and tablets containing from 200 mg to 1 g of paracetamol were then prepared.

The release test, accomplished according to USP XXI, Apparatus No. 2, at 50 rpm and with 900 ml of juice of pH 5.8, showed the following release results:
1st hour = 22.8%
4th hour = 54.6%
8th hour = 98.3%.

The release rate was increased or decreased by proportionally varying the amount of the applied membrane. It should be noted that instead of a Loedige type mixer, a fluid bed or stainless steel coating pan may be used and with the same membrane comparative results may be obtained.

EXAMPLE 3

Operating as described in Example 2, but applying only the 10% of membrane, tablets were obtained showing a very rapid release. With a further coating of the tablets in the stainless steel pan using from 10 to 20% of the same membrane, the following release profile was obtained:
1st hour = 10-25%
4th hour = 40-80%
8th hour = 70-100%.

EXAMPLE 4

Operating as described in Example 1, on 34.40 kg of inert granules (size 0.7-1 mm) 49.50 kg of propanolol HCl were applied with 11.00 kg of a 20% (w/w) ethanolic solution of polyvinylpyrrolidone (k value = 30).

The membranes were applied in successive layers for a total weight of 8.10 kg of paraffin previously melted and diluted to a 40% concentration with methylene chloride at a temperature of 30°-45° C.

The methacrylic acid copolymers (Rohm Pharma, Eudragit E and RS type) were applied in acetonic solution. The end amounts were as follows:
Eudragit RS kg 0.60;
Eudragit E kg 0.30.

During the application of the successive layers 4.80 kg of talc were added.

The release test, carried out according to USP XXI, Apparatus No. 1, at 100 rpm and with 900 ml of juice of pH 1.2 for the first hour and of 7.5 for fourth and eighth hour, gave the following results:
1st hour = 13.3%;
4th hour = 47.2%;
8th hour = 82.8%.

After administration of a capsule containing 160 mg of propranolol HCl, the in vivo results showed a pharmacologically active blood level for 24 hours as the known product Inderal LA available in Switzerland, England, etc. With the above formulation, capsules containing from 40 to 250 mg of propranolol HCl may be prepared.

EXAMPLE 5

Operating as described in Example 4 but with the following per cent composition on dried microgranules

| | |
|---|---|
| diltiazem HCl | 43.6% |
| neutral granules | 22.5% (size 0.7-1 mm) |
| paraffin (USP XXI, page 1584) | 13.0% |
| Polyvinylpyrrolidone (USP XXI, page 1584) | 8.8% |
| Eudragit E (Rohm Pharma) | 2.1% |

| -continued | |
|---|---|
| Eudragit RS (Rohm Pharma) | 0.8% |
| talc | 9.2% | the analysis, performed according to USP XXI, Apparatus No. 1, at 100 rpm and in 800 ml of HCl N/10, provided the results reported in Table 2, curve D. The other curves were obtained by increasing or decreasing the membrane amount in comparison with that indicated above. These different release rates were guaranted by a very good reproducibility.

With the above indicated formulation, capsules containing from 50 to 250 mg of diltiazem can be obtained.

EXAMPLE 6

69.30 kg of neutral microgranules (granular size 0.9-1.1 mm) were placed in a stainless steel pan and 23.00 kg of isosorbide-5-mononitrate were applied after dissolution in 20.00 kg of acetone and 45.00 kg of methylene chloride in which 0.95 kg of ethylcellulose (ethoxy groups 44.5-50%) were dissolved.

After drying, the membrane was applied from ethanolic solution. The dried microgranules contained 6.05 kg of ethylcellulose, 0.655 kg of stearic acid (NF XVI, page 1611) and 85 g of talc. The analysis according to USP XXI, Apparatus No. 2, at 100 rpm and with 1000 ml of juice of pH 7.5, provided the following release results:
1st hour=29.7%
4th hour=70.4%
8th hour=88.7%.

The studies on 8 volunteers with 50 mg capsules, in comparison with the known product Elantan Long, available in Germany, showed a very good bioequivalence with a posology of one daily capsule.

With the above formulation, capsules containing from 20 to 120 mg of isosorbide-5-mononitrate may be prepared.

EXAMPLE 7

Operating as described in Example 6, but with the following per cent composition:

| phenylpropanolamine HCl | 31.6% | |
|---|---|---|
| neutral granules | 56.5% | (0.7-1 mm) |
| polyvinylpyrrolidone | 2.0% | (k value = 30) |
| ethylcellulose | 7.7% | (ethoxy groups 44.5-50%) |
| stearic acid (NF XVI, page 1611) | 0.7% | |
| talc | 1.5% | | the analysis according to USP XXI, Apparatus No. 1, at 100 rpm, with 500 ml of distilled water, gave the following results:
1st hour=51.8%
2nd hour=72.2%
4th hour=96.4%

The percent release was the same as for the known product Dexatrin, available in Switzerland and U.S.A.- With the above described formulation capsules containing from 10 to 150 mg may be prepared.

EXAMPLE 8

On 33.00 kg of neutral microgranules, prepared as described in Example 1, 40.00 kg of diacerheyn were applied using a binding agent comprising a solution containing 10.20 kg of polyethylene glycol 4000 and 40.00 kg of ethanol, After drying, a membrane comprising 42.20 kg of ethanol, 2.20 kg of ethylcellulose (ethoxy groups 44.5-50.0%) and 0.500 kg of stearic acid was applied in solution. The test was performed according to USP XXI, Apparatus No. 2, at 100 rpm, with 900 ml of juice of pH 7.5 added with 0.05% (w/w) of Tween 80, and it gave the following results:
1st hour=47%
4th hour=73%
8th hour=88%
12th hour=94%

EXAMPLE 9

93.00 kg of theophylline were placed in a granulator together with a solution containing 3.50 kg of polyvinylpyrrolidone (k value=30) and 14.00 kg of ethanol. After drying, the granulate was sieved and only the fractions having a granular size of 500 to 800 microns were retained. The other finer and coarser fractions were applied after micronization, in a coating pan, on selected nuclei with a binding solution containing 3.50 kg of polyvinylpyrrolidone (k value=30) and 28.00 kg of ethanol.

After drying, on 10.00 kg of microgranules a solution comprising 0.84 kg of ethylcellulose (44.5-50.0% ethoxy groups) and 84 g of stearic acid in 16.00 kg of ethanol was applied.

The release test carried out according to USP XXI, Apparatus No. 1, at 125 rpm, with 900 ml of distilled water, provided the following results:
1st hour=12.7%
2nd hour=22.5%
4th hour=37.6%
6th hour=49.1%
8th hour=58.2%
12th hour=71.0%
16th hour=82.3%.

EXAMPLE 10

On 10.00 kg of microgranules, obtained by granulation as described in Example 9, a solution containing 0.40 kg of hydroxypropylmethylcellulose (50 cps) and 0.40 kg of stearic acid was applied.

The release test performed as in Example 9 gave the following results:
1st hour=7.6%
2nd hour=21.9%
4th hour=45.5%
6th hour=61.4%
8th hour=72.1%
12th hour=86.5%
16th hour=93.9%.

EXAMPLE 11

On 10.00 kg of microgranules, obtained by granulation as described in Example 9, a solution containing 0.35 kg of methacrylic acid copolymer (Eudragit RS) and 0.35 kg of stearic acid in 3.50 kg of acetone and 3.50 kg of ethanol was applied.

The release test carried out as in Example 9, provided the following release profile:
1st hour=24.5%
2nd hour=47.1%
4th hour=71.5%
6th hour=82.1%
8th hour=87.8%
12th hour=94.0%

I claim:

1. A pharmaceutical oral controlled release composition comprising a multiplicity of small pellets consisting of microgranules of inert material, a medicament layer applied thereon and a coating membrane applied upon the medicament layer, said coating membrane being a mixture of stearic acid and ethylcellulose or of paraffin and methacrylic acid copolymers, characterized in that the medicament is selected from the group consisting of ketoprofen, paracetamol, propranolol, diltiazem, isosorbide-5-mononitrate, phenylpropanolamine and diacerheyn, stearic acid and paraffin being present in an amount ranging from 0.7% to 16% and ethylcellulose and methacrylic acid copolymer being present in an amount ranging from 0.3% to 26.3%, based on the medicament weight respectively, and in that the medicament sustained release in vitro achieved is of from 4 to 22 hours or longer.

2. A pharmaceutical composition according to claim 1, wherein the medicament is selected from the group consisting of ketoprofen, paracetamol, isosorbide-5-mononitrate, phenylpropanolamine and diacerheyn, and the coating membrane comprises a mixture of stearic acid and ethylcellulose.

3. A pharmaceutical composition according to claim 1, wherein the medicament is selected from the group consisting of propranolol and diltiazem and the coating membrane comprises a mixture of paraffin and methacrylic acid copolymer.

4. A pharmaceutical composition according to claim 1, wherein the medicament is ketoprofen and the coating membrane comprises 4.16% by weight of stearic acid and 2.48% by weight of ethylcellulose.

5. A pharmaceutical composition according to claim 1, wherein the medicament is paracetamol and the coating membrane comprises 15.12% by weight by stearic acid and 3.05% by weight of ethylcellulose.

6. A pharmaceutical composition according to claim 1, wherein the medicament is isosorbide-5-mononitrate and the coating membrane comprises 2.84% by weight of stearic acid and 26.3% by weight of ethylcellulose.

7. A pharmaceutical composition according to claim 1, wherein the medicament is phenylpropanolamine and the coating membrane comprises 0.7% by weight of stearic acid and 7.7% by weight of ethylcellulose.

8. A pharmaceutical composition according to claim 1, wherein the medicament is diacerheyn and the coating membrane comprises 1.25% by weight of stearic acid and 5.5% by weight of ethylcellulose.

9. A pharmaceutical composition according to claim 1, wherein the medicament is propranolol and the coating membrane comprises 16.36% by weight of paraffin and 1.81% by weight of methacrylic acid copolymers.

10. A pharmaceutical composition according to claim 1, wherein the medicament is diltiazem and the coating membrane comprises 13% by weight of paraffin and 2.9% by weight of methacrylic acid copolymers.

11. A process for preparing a pharmaceutical oral controlled release composition according to claim 2, comprising coating microgranules of inert material with a medicament layer and applying a coating membrane upon said medicament layer, the medicament being soluble and selected from the group consisting of ketoprofen, paracetamol, propranolol, diatiazem, isosorbide-5-mononitrate, phenylpropanolamine and diacerheyn, and the coating membrane being a mixture of stearic acid and ethylcellulose or of paraffin and methacrylic acid copolymers.

12. The process according to claim 11, wherein the coating membrane is applied from a solution containing both the components stearic acid/ethylcellulose or paraffin/methacrylic acid copolymer.

13. The process of claim 11, wherein the coating membrane is applied in alternate and separate layers while in a melted state.

* * * * *